(12) United States Patent
Conner et al.

(10) Patent No.: US 8,795,993 B2
(45) Date of Patent: Aug. 5, 2014

(54) PROCESS FOR TREATING BIOMASS TO DERIVATIZE POLYSACCHARIDES CONTAINED THEREIN TO INCREASE THEIR ACCESSIBILITY TO HYDROLYSIS AND SUBSEQUENT FERMENTATION

(75) Inventors: Herbert T. Conner, Landenberg, PA (US); Patrick J. Cowan, Hockessin, DE (US); John C. Gast, Hockessin, DE (US)

(73) Assignee: Hercules Incorporated, Wilmington, DE (US)

( * ) Notice: Subject to any disclaimer, the term of this patent is extended or adjusted under 35 U.S.C. 154(b) by 1012 days.

(21) Appl. No.: 12/699,584

(22) Filed: Feb. 3, 2010

(65) Prior Publication Data

US 2011/0039309 A1 Feb. 17, 2011

Related U.S. Application Data

(60) Provisional application No. 61/206,742, filed on Feb. 3, 2009.

(51) Int. Cl.
| | | |
|---|---|---|
| *C12P 7/06* | (2006.01) | |
| *C12P 7/10* | (2006.01) | |
| *C12P 7/16* | (2006.01) | |
| *C12P 1/00* | (2006.01) | |
| *A61K 31/045* | (2006.01) | |
| *C12P 1/06* | (2006.01) | |
| *C12P 19/14* | (2006.01) | |
| *C12P 7/56* | (2006.01) | |
| *C12P 7/46* | (2006.01) | |
| *C12P 7/42* | (2006.01) | |

(52) U.S. Cl.
USPC ............ 435/160; 424/438; 435/68.1; 435/99; 435/139; 435/146; 435/148; 435/158; 435/165; 435/167; 514/554; 514/557

(58) Field of Classification Search
USPC ........... 435/41, 105, 147, 148, 157, 160, 161, 435/68.1, 99, 126, 128, 139, 146, 158, 165, 435/167, 168; 536/124; 424/438; 514/554, 514/557
See application file for complete search history.

(56) References Cited

U.S. PATENT DOCUMENTS

| 3,093,629 | A | * | 6/1963 | Fugate et al. ............... 536/44 |
| 5,846,787 | A | | 12/1998 | Ladisch et al. |
| 5,916,780 | A | | 6/1999 | Foody et al. |
| 6,602,994 | B1 | | 8/2003 | Cash et al. |
| 2007/0031918 | A1 | | 2/2007 | Dunson, Jr. et al. |

FOREIGN PATENT DOCUMENTS

| WO | 00/08059 | 2/2000 |
| WO | 00/47628 | 8/2000 |

OTHER PUBLICATIONS van Dijken et al., 1986. Redox balances in the metabolism of sugars by yeasts. FEMS Microbiology Reviews., vol. 32, pp. 199-224.*
Sigfried et al. 2001. Ullman's Encyclopedia of Industrial Chemistry, vol. 13, pp. 547-772, p. 553, col. 1, Lines 29-36.*
Touzinsky et al 1979.. Degree of substitution of cellulose derrivatives containing n different substituent groups. Carbohydrate Research vol. 69, pp. 327-329.*
Zhang et al. 2006. Outlook for cellulase improvement: Screening and selection strategies. Biotechnology Advances, vol. 24, pp. 452-481.*
Zverlov et al. 2006. Bacterial acetone and butanol production by industrial fermentation in the Soviet Union: use of hydrolyzed agricultural waste for biorefinery. Applied Microbiology and Biotechnology, vol. 71, pp. 587-597.*
International Search Report, Form PCT/ISA/210, Jul. 12, 2010, pp. 1-4.
Borsa, J.; Tanczos, I.; Ruszak, I.; Acid Hydrolysis of Carboxymethylcellulose of Low Degree of Substitution, Colloid and Polymer Science, vol. 268 No. 7, 649-857 (1990).
Zhao, et al., Enhanced Enzymatic Hydrolysis of Spruce by Alkaline Pretreatment at Low Temperature, Biotechnology and Bioengineering, vol. 99, No. 6, 1320-1328 (2008).

\* cited by examiner

*Primary Examiner* — Jon P Weber
*Assistant Examiner* — Kailash C Srivastava
(74) *Attorney, Agent, or Firm* — Shaorong Chen (57) ABSTRACT

A process is described for producing fermentable sugars derivable from biomass that contains polysaccharide, such as cellulose, made increasingly accessible as a substrate for enzymatic degradation or other methods of depolymerization. These fermentable sugars are subsequently able to be fermented to produce various target chemicals, such as alcohols, aldehydes, ketones or acids.

34 Claims, 1 Drawing Sheet

PROCESS FOR TREATING BIOMASS TO DERIVATIZE POLYSACCHARIDES CONTAINED THEREIN TO INCREASE THEIR ACCESSIBILITY TO HYDROLYSIS AND SUBSEQUENT FERMENTATION

RELATED APPLICATIONS

This application claims the benefit of U.S. Provisional Application Ser. No. 61/206,742, filed on Feb. 3, 2009, the disclosure of which is incorporated herein by reference in its entirety.

FIELD OF THE INVENTION

This invention relates to polysaccharides, particularly to cellulose, and to a process for converting polysaccharide to sugars which can be subsequently fermented.

BACKGROUND OF THE INVENTION

Polysaccharides contain structured and even crystalline portions which make them less soluble in water and also difficult to break down to their recurring units to obtain the underlying monomeric units. In the case of cellulose, these monomeric units are glucose units which can be converted to useful compounds, including ethanol or similar alcohols obtained through fermentation.

Ethanol and other chemical fermentation products typically have been produced from sugars derived from high value feedstocks which are typically high in starches and sugars, such as corn. These high value feedstocks also have high value as food or feed.

It has long been a goal of chemical researchers to improve the efficiency of depolymerizing polysaccharides to obtain monomeric and/or oligomeric sugar units that make up the polysaccharide repeating units, it is desirable to increase the rate of reaction to yield free monomer and/or oligomers units in order to increase the amount of alcohol that may be obtained by fermentation of the monomeric and/or oligomeric units.

Much research effort has been directed toward enzymes for depolymerizing polysaccharides, especially to obtain fermentable sugars which can be converted by fermentation to target chemicals such as alcohols.

However, some polysaccharides, such as cellulose, are relatively resistant to depolymerization due to their rigid, tightly bound crystalline chains. Thus the rate of hydrolysis reaction to yield monomer may be insufficient for use of these polysaccharides in general and cellulose in particular as a source for saccharide monomers in commercial processes. Enzymatic hydrolysis and fermentation in particular can also take much longer for such polysaccharides. This in turn adversely affects the yield and the cost of fermentation products produced using polysaccharides as substrates A number of methods have been developed to weaken the ordered regions of polysaccharides to obtain more efficient monomer release. Most of these methods involve pre-treatment of the polysaccharide prior to reactions to obtain monomers. Pretreatments chemically and/or physically help to overcome resistance to enzymatic hydrolysis and are used to enhance cellulase action. Physical pretreatments for plant lignocellulosics include size reduction, steam explosion, irradiation, cryomilling, and freeze explosion. Chemical pretreatments include dilute acid hydrolysis, buffered solvent pumping, alkali or alkali/$H_2O_2$ delignification, solvents, ammonia, and microbial or enzymatic methods.

These methods include acid hydrolysis, described in U.S. Pat. No. 5,918,780 to Foody, et al. The referenced patent also describes the deficiency of acid hydrolysis and teaches use of pretreatment and treatments by enzymatic hydrolysis.

U.S. Pat. No. 5,846,787 to Ladisch, et al. describes enzymatically hydrolyzing a pretreated cellulosic material in the presence of a cellulase enzyme where the pretreatment consists of heating the cellulosic material in water.

In US Patent Application No. 20070031918 A1, a biomass is pretreated using a low concentration of aqueous ammonia at high biomass concentration. The pretreated biomass is further hydrolyzed with saccharification enzymes wherein fermentable sugars released by saccharification may be utilized for the production of target chemicals by fermentation.

Zhao, et. al. (Zhao, Y. Wang, Y, Zhu, J. Y., Ragauskas, A., Deng, Y. in Biotechnology and Bioengineering (2008) 99(6) (1320-1328)) have shown that high levels of urea, when combined with sodium hydroxide as a means of swelling the cellulosic matrix, improves the accessibility of the isolated cellulose for subsequent enzymatic hydrolysis. This may be attributed to the effect of the urea in disrupting the hydrogen bonding structures that are important in producing the more ordered regions of the polysaccharide.

Borsa, et al. (J. Borsa, I. Tanczos and I. Rusznak, "Acid Hydrolysis of Carboxymethylcellulose of Low Degree of Substitution", Colloid & Polymer Science, 268:849-657 (1990)) has shown that introduction of very low levels of carboxymethylation accelerates the initial rate of hydrolysis when cellulose is subjected to acid hydrolysis.

The process taught in Borsa et al. treats cotton fabrics by dipping in caustic and then sodium chloroacetate solution resulting in mild surface substitution at levels below 0.1 D.S. This is illustrated in FIG. 1 of Borsa et al. which shows a maximum D.S. of about 95 millimoles per basemole after 20 minutes of carboxymethlation, or 0.095 D.S. if using the numbering for D.S. as carboxymethyl groups per anhydroglucose unit.

Borsa et al. used a large excess sodium hydroxide (of mercerizing strength) but a small amount of chloroacetic acid. Further, reported yields in Borsa, et al. of hydrolyzate are on the order of 0 to 35 milligrams per gram, or not more than 3.5% while the untreated cotton control yields about 2.5% hydrolysis under the same conditions.

In U.S. Pat. No. 6,602,994 to Cash, et al., it has been shown that low levels of cellulosic derivatization aids in reducing the amount of mechanical energy required for defibrillation. Cellulose is first swelled with alkali and then reacted with chloroacetic acid or other suitable reagents to obtain derivatized cellulose.

SUMMARY OF THE INVENTION

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range, it is not intended that the scope of the invention be limited to the specific values recited when defining a range.

In this invention a process is described that makes biomass that contains polysaccharide, such as cellulose, increasingly accessible as a substrate for enzymatic degradation, or other methods of depolymerization.

One aspect of the present invention relates to a process for producing fermentable sugars derivable from biomass that contains polysaccharide. The process comprises the steps of obtaining a biomass that contains polysaccharide; treating the biomass with a swelling agent; contacting the biomass with a derivatization agent to produce a derivatized polysaccharide with increased accessibility and wherein the derivatized polysaccharide with increased accessibility is substantially insoluble as measured by the solubility test. The derivatized polysaccharide with increased accessibility may be used as a substrate for enzymatic hydrolysis or other methods of depolymerization, and so that the derivatized polysaccharide remains substantially insoluble in the medium conducive to enzymatic hydrolysis or other methods of depolymerization. The derivatized polysaccharide with increased accessibility is converted to fermentable sugars by hydrolysis, such as through the use of one or more saccharification enzymes or acid hydrolysis.

The derivatized polysaccharide with increased accessibility exhibits greater solubility using an Enzyme Accessibility Test when compared to polysaccharide obtained from the biomass containing polysaccharide which has been treated with the swelling agent but has not been contacted with the derivatization agent.

Another aspect of the present invention is a process for converting polysaccharide into fermentable sugars which can then be treated with at least one biocatalyst able to ferment the sugars converted to produce the target chemical under suitable fermentation conditions. The conversion process comprising the steps of obtaining a biomass containing polysaccharide and treating the biomass in a media with a swelling agent. The polysaccharide contained in the biomass is derivatized by addition of a derivatization agent that reacts with the hydroxyl, carboxyl, or other functional groups of the polysaccharide.

While not wishing to be bound by theory, a "derivatized polysaccharide with increased accessibility" is a polysaccharide in which the ordered structure of the polysaccharide is rendered less ordered by reacting within the matrix of the polysaccharide molecular structure with derivatization agents that interrupt the ability of the polysaccharide to return to an ordered structure upon removal or neutralization of the swelling agent from the polysaccharide. Reduction of order in the polysaccharide is obtained without substantially altering the molecular order of the polysaccharide, that is, without substantially altering the anhydro-ring structure that is inherent to the polysaccharide molecular structure.

In a one aspect of the invention, the polysaccharide in the biomass is contacted with a swelling agent having sufficient alkalinity to swell of the polysaccharide. Alkalinity can be provided by treatment with an alkaline solution or vapor with sufficient alkalinity to swell the polysaccharide. The swelling agent may be present in a media wherein the media in which the swelling agent is contained may be in liquid form and may be any alkaline solution comprising water, water-miscible solvent such as alcohol or acetone, water/alcohol mixtures or water-miscible solvent such as alcohol or acetone, if the media which the swelling agent is contained is in a vapor form, it may comprise either air or other readily obtainable or generated gas.

The swelling agent may be removed from the biomass containing polysaccharide or neutralized prior to subsequent conversion to fermentable sugars in order not to inhibit or interfere with effectiveness of the one or more saccharification enzymes used to produce the fermentable sugars from the polysaccharide.

In yet another aspect of the invention, an effective amount of the derivatization agent is retained within biomass that contains polysaccharide upon removal or neutralization of the swelling agent by chemical reaction with the polysaccharide.

Derivatization agents that effectively reduce the order the polysaccharide following incorporation into the polysaccharide and which are retained following removal of the swelling agent include but are not limited to materials known to react with the hydroxyl, carboxyl, or other functional groups of the polysaccharide under conditions of swelling, including but not limited to chloroacetic acid, sodium chloroacetate, ethylene oxide, and other well known polysaccharide derivatizing agents.

In another aspect of the invention, derivatized polysaccharide with increased accessibility is then treated to remove or neutralize the swelling agent. Various methods are available for removing or neutralizing the swelling agent. In a specific example an alkaline swelling agent is pH adjusted to a level suitable for a subsequent conversion of the derivatized polysaccharide with increased accessibility to monomer or oligomer units by enzymatic hydrolysis. The derivatized polysaccharide with increased accessibility is converted to monomeric and/or oligomeric sugar units by enzymatic hydrolysis, and these available monomeric and/or oligomeric sugar units may now be converted into various desirable target chemicals by fermentation or other chemical processes.

In a specific aspect of the invention, the polysaccharide is reacted with a derivatizating agent to a desired degree of substitution between about 0.01 and 3.0, forming a substantially insoluble derivatized polysaccharide, as determined by the solubility test. The media containing the polysaccharide is then pH adjusted to a level suitable for a subsequent conversion of the derivatized polysaccharide with increased accessibility. The derivatized polysaccharide with increased accessibility is converted to fermentable sugars by hydrolysis, and these available fermentable sugars may now be converted into various desirable target chemicals by fermentation or other chemical processes.

In the process of the present invention, polysaccharide can be derivatized to a desired degree of substitution (D.S.) of about 0.01 to 3.0 to form the substantially insoluble derivatized polysaccharide with increased accessibility while maintaining the polysaccharide as substantially insoluble.

In another aspect of the invention, a process to obtain fermentable sugars from a polysaccharide in which the polysaccharide is treated with a derivatizing agent, such as chloroacetic acid, under alkaline conditions to produce a derivatized polysaccharide with increased accessibility, where such a derivatized polysaccharide with increased accessibility would comprise a polysaccharide ether having a Degree of Substitution (D.S.) between about 0.01 and 3.0, more preferred, about 0.01 to 1.2, and most preferred about 0.01 to 0.4. While not wishing to be bound by theory, it is believed that this derivatization process disrupts ordered areas in the polysaccharide, resulting in a polysaccharide with increased accessibility and making the monomeric or oligomeric units of the derivatized polysaccharide with increased accessibility more available for hydrolysis.

The derivatized polysaccharide with increased accessibility produced by the above mentioned process can be treated with a saccharification enzyme or enzymes, such as cellulase enzyme, under suitable conditions to produce fermentable sugars. This hydrolytic degradation depolymerizes the derivatized polysaccharide making the monomeric and oligomeric units which comprise the fermentable sugars available for a number of uses, including production of target chemicals by fermentation.

In a further aspect of the invention, the products arising from hydrolysis of the derivatized polysaccharide, which contain the monomeric and oligomeric units, is then treated with a yeast or related organism or enzyme under suitable fermentation conditions to induce enzymatic degradation of the monomeric and/or oligomeric units such as fermentation. Fermentation breaks bonds in the sugar rings and results in the monomer or oligomer units being converted to target chemicals. The target chemicals obtained from the above described process may be selected from the group consisting of alcohols, aldehydes, ketones and acids. The alcohols produced by the above described process may include the group consisting of methanol, ethanol, propanol, 1,2 propanediol, glycerol, and butanol. The preferred alcohol being ethanol.

DETAILED DESCRIPTION OF THE INVENTION

One aspect of this invention relates to a process that makes a biomass that contains polysaccharide, such as cellulose, increasingly accessible as a substrate for enzymatic degradation or other methods of depolymerization. In one example, this is achieved by forming a derivatized polysaccharide with increased accessibility following treatment with a swelling agent and a derivatization agent that reacts within the polysaccharide matrix. The swelling agent may then be subsequently removed or neutralized. The derivatized polysaccharide exhibits increased accessibility upon reaction of the derivatization agent within the polysaccharide structure.

Another aspect of this invention relates to a process for preparation of target chemicals from polysaccharide substrates with increased accessibility in which said processes comprises, in combination or sequence, hydrolysis of the derivatized polysaccharide substrates with increased accessibility to fermentable sugars and enzymatic degradation of such fermentable sugars such as occurs in fermentation or other chemical processes, such as acid hydrolysis.

In this disclosure, a number of terms are used. The following definitions are provided.

The term "fermentable sugar" refers to oligosaccharides, monosaccharides, and other small molecules derived from polysaccharides that can be used as a carbon source by a microorganism, or an enzyme, in a fermentation process.

The term "lignocellulosic" refers to a composition or biomass comprising both lignin and cellulose. Lignocellulosic material may also comprise hemicellulose.

The term "cellulosic" refers to a composition comprising cellulose.

The term "target chemical" refers to a chemical produced by fermentation or chemical alteration from a derivatized polysaccharide rendered to be more accessible by the processes of this invention. Chemical is used in a broad sense and includes molecules such as proteins, including, for example, peptides, enzymes and antibodies.

The term "saccharification" refers to the production of fermentable sugars from polysaccharides.

The phrase "suitable conditions to produce fermentable sugars" refers to conditions such as pH, composition of medium, and temperature under which saccharification enzymes are active.

The phrase "suitable fermentation conditions" refers to conditions that support the growth and target chemical production by a biocatalyst. Such conditions may include pH, nutrients and other medium components, temperature, atmosphere, and other factors.

The term "degree of substitution" (D.S.) means the average number of hydroxyl groups, per monomer unit in the polysaccharide molecule which have been substituted. For example in cellulose, if on average only one of the positions on each anhydroglucose unit are substituted, the D.S. is designated as 1, if on average of two of the positions on each anhydroglucose unit are reacted, the D.S. is designated as 2. The highest available D.S. for cellulose is 3, which means each hydroxyl unit of the anhydroglucose unit is substituted.

The term "molar substitution" (M.S.) refers to the average number of moles of substituent groups per monomer unit of the polysaccharide.

The term "derivatized polysaccharide with increased accessibility" refers to polysaccharides exhibiting increased accessibility to enzyme as determined using the Enzyme Accessibility Test.

The term "substantially insoluble" refers to polysaccharides exhibiting less than a 75% soluble portion in the solubility test.

The term "biomass" refers to material containing polysaccharide such as any cellulosic or lignocellulosic materials and includes materials comprising polysaccharides, such as cellulose, and optionally further comprising hemicellulose, lignin, starch, oligosaccharides and/or monosaccharides. Biomass may also comprise additional components, such as protein and/or lipid. According to the invention, biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, cotton, cotton linters, switchgrass, waste or post consumer paper, waste or post consumer paperboard, sugar cane bagasse, sorghum, soy, components obtained from milling of grains, trees, branches, roots, leaves, wood chips, sawdust, shrubs and bushes, vegetables, fruits, flowers and animal manure, in one embodiment, biomass that is useful for the invention includes biomass that has a relatively high carbohydrate value, is relatively dense, and/or is relatively easy to collect, transport, store and/or handle. In one embodiment of the invention, biomass that is useful includes corn cobs, corn stover and sugar cane bagasse.

The biomass may also comprise various suitable polysaccharides which include, chitin, chitosan, guar gum, pectin, alginate, agar, xanthan, starch, amylose, amylopectin, alternan, gellan, mutan, dextran, pullulan, fructan, locust bean gum, carrageenan, glycogen, glycosaminoglycans, murein, bacterial capsular polysaccharides, and derivatives thereof. Mixtures of these polysaccharides may be employed. Preferred polysaccharides are cellulose, chitin, chitosan, pectin, agar, starch, carrageenan, and derivatives thereof, used singly or in combination, with cellulose being most preferred. The cellulose may be obtained from any available source, including, by way of example only, chemical pulps, mechanical pulps, thermal mechanical pulps, chemical-thermal mechanical pulps, recycled fibers, newsprint, cotton, soybean hulls, pea hulls, corn hulls, flax, hemp, jute, ramie, kenaf, manila hemp, sisal hemp, bagasse, corn, wheat, bamboo, velonia, bacteria, algae and fungi. Other sources of cellulose include purified, optionally bleached wood pulps produced from sulfite, kraft, or prehydrolyzed kraft pulping processes: purified cotton linters; fruits; and vegetables. Cellulose containing materials most often include lignin and are often referred to as lignocellulosics, which include the various wood, grass, and structural plant species found throughout the plant world, many of which are mentioned above. The biomass may be used directly as obtained from the source, or energy may be applied to the biomass to reduce the size, increase the exposed surface area, and/or increase the availability of polysaccharides present in the biomass. Energy means useful for reducing the size, increasing the exposed surface area, and/or increasing the availability of cellulose, hemicellulose, and/or oligosaccharides present in the biomass include, but are not limited to, milling, crushing, grinding, shredding, chopping, disc refining, ultrasound, and microwave. This application of energy may occur before or during pretreatment, before or during saccharification, or any combination thereof.

Conditions for swelling polysaccharides should generally include, but are not limited to, treatment with an alkaline agent producing swelling of the polysaccharide. The swelling process is intended to make the polysaccharide more accessible to the reaction of the derivatization agent within the polysaccharide matrix. Swelling may be provided to various degrees and may involve treatment with one or more materials, in particular, alkaline agents often serve multiple purposes, in that they may swell the polysaccharide and also may solubilize and transport the derivatization agent into the swollen polysaccharide matrix. The swelling agents may also catalyze the reaction between the polysaccharide and the derivatization agent.

Alkaline conditions are preferably obtained by using sodium hydroxide. Any material that functions as an alkaline media for the polysaccharide of choice may be used as a swelling agent, and alternative swelling agents include alkali metal or alkaline earth metal oxides or hydroxides; alkali silicates; alkali aluminates; alkali carbonates; amines, including aliphatic hydrocarbon amines, especially tertiary amines; ammonia, ammonium hydroxide; tetramethyl ammonium hydroxide; lithium chloride; N-methyl morpholine N-oxide; and the like. In addition to catalytic amounts of swelling agent, swelling agents may be added to increase access for derivatization.

The concentration of the swelling agent can be at various levels though the general result is that higher levels of swelling agent will produce more opportunity for incorporation of the derivatization agent. In particular if swelling agents such as those produced by the alkali metal hydroxides are used than concentrations that produce a significant degree of swelling, such as levels that produce relatively uniformly substituted cellulose derivatives, up to and including the so-called mercerization condition for cellulose, provide for opportunities for improved incorporation of the derivatization agent.

The form of the swelling agent can also be of various types well known to those skillful in swelling polysaccharides. Most common are aqueous solutions of an alkaline material but also used are combinations of water and other solvents such as alcohols, acetone, or miscible solvents to form so-called slurries of swollen polysaccharides. Employing different types and ratios of cosolvents can produce various degrees of disorder in the final product after removal or neutralization of the swelling agent. Yet another common form of swelling agent would include penetrating gases such as ammonia which are capable of swelling polysaccharides under specific conditions.

Materials useful for disrupting the order of the polysaccharide can be of various types, as long as said derivatization agent can be reacted with the polysaccharide by a number of various processes. These derivatization agents act to produce a product with increased accessibility for subsequent reactions or treatment with various materials.

"Derivatization" refers to chemical reactions resulting in covalent bonds formed within the polysaccharide, making the derivatized polysaccharide more accessible as a substrate for enzymatic degradation or other methods of depolymerization.

Preferred derivatized polysaccharides that may be obtained using cellulose include, but are not limited to, hydroxyethyl cellulose, ethylhydroxyethyl cellulose, carboxymethylcellulose, carboxymethylhydroxyethyl cellulose, hydroxypropylhydroxyethyl cellulose, methyl cellulose, methylhydroxypropyl cellulose, methylhydroxyethyl cellulose, carboxymethylmethyl cellulose, hydrophobically modified carboxymethylcellulose, hydrophobically modified hydroxyethyl cellulose, hydrophobically modified hydroxypropyl cellulose, hydrophobically modified ethylhydroxyethyl cellulose, hydrophobically modified carboxymethylhydroxyethyl cellulose, hydrophobically modified hydroxypropylhydroxyethyl cellulose, hydrophobically modified methyl cellulose, hydrophobically modified methylhydroxypropyl cellulose, hydrophobically modified methylhydroxyethyl cellulose, hydrophobically modified carboxymethylmethyl cellulose, nitrocellulose, cellulose acetate, cellulose sulfate, cellulose vinyl sulfate, cellulose phosphate, and cellulose phosphonate. Other polysaccharides may be similarly derivatized.

The derivatization may be carried out in any suitable manner including, but not limited to, suspension in water; in organic solvent, either alone or in mixtures with water; in solution; and in high solids, either with water alone or with water and a minor amount of organic solvent. (For purposes of the present disclosure, "high solids" refers to a polysaccharide content of greater than about 25%).

The derivatized polysaccharides useful in this invention have a degree of substitution (D.S.) of between about 0.01 and 3.0, more preferred, about 0.01 to 1.2, and most preferred about 0.01 to 0.4.

A preferred derivatization agent comprises chloroacetic acid, also referred to as monochloroacetic acid (MCA). When MCA is reacted with cellulose, the resultant derivatized product comprises carboxymethyl cellulose. Another preferred disrupting agent comprises sodium chloroacetate, which, when reacted with cellulose, also produces carboxymethyl cellulose. A preferred polysaccharide with increased accessibility comprises a carboxymethylcellulose that has a degree of substitution (D.S.) of between about of 0.01 to 0.6.

Other derivatization agents include but are not limited to ethylene oxide, propylene oxide, methyl chloride and other alkyl halides, anhydrides, aldehydes, compounds containing quaternary cation functionality, epichlorhydrin, and other materials known to derivatize polysaccharides. The derivatized polysaccharides may have a molar substitution of less than about 3.0, or of less than about 1.5, or of less than about 1.0, or of less than about 0.5. The range of molar substitution may be from about 0.5 to about 3.0. Molar substitution may be provided, by way of non-limiting example, by hydroxyethyl groups, hydroxypropyl groups, methyl groups, ethyl groups; straight- or branched-chain alkyl, alkenyl, or alkynyl groups having from about 4 to about 30 carbons; and/or aryl, arylalkyl, arylalkenyl, cyclic, and heterocyclic hydrocarbons having from about 4 to about 30 carbons.

In certain cases, one may be able to utilize the resultant target chemical as a raw material for the production of the derivatization agent whereby a portion of the target chemical is converted into the derivatization agent; and then a portion of the derivatization agent converted from the target chemical is fed back in the process to contact the biomass as a derivatization agent.

Of particular interest is the use of ethylene oxide as the derivatization agent since one may be able to utilize the resultant target chemical, ethanol, as a source material for the production of ethylene oxide which can be fed back into the process as the derivatization agent for production of hydroxyethylcellulose. A preferred polysaccharide with increased accessibility comprises a hydroxyethylcellulose that has a molar substitution (M.S.) in a range of from about 0.05 to about 2.0.

Figure 1:
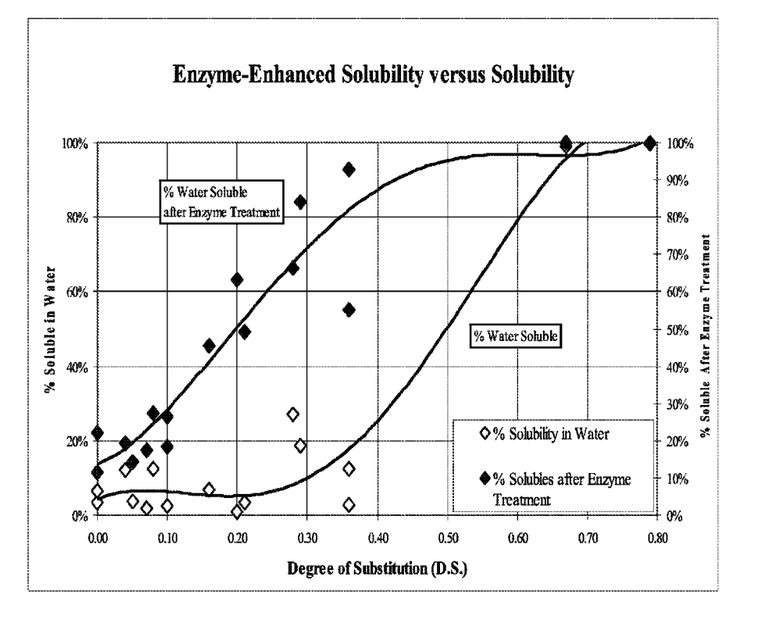
FIG. 1 is graph depicting the percentage of soluble polysaccharide after enzyme treatment versus solubility of the polysaccharides in water at various levels of D.S.

An unexpected benefit of the process of the present invention is demonstrated in FIG. 1. In FIG. 1, it is shown that the increase in accessibility of derivatized cellulose to enzyme occurs at a lower level of derivatization than its solubility in water. This difference between the derivatized polysaccharide with increased accessibility, and its solubility, is a benefit of the present invention for it allows for production of derivatized polysaccharides with increased accessibility to hydrolysis, while maintaining the derivatized polysaccharide in a relatively insoluble state. Derivatized polysaccharide with increased accessibility exhibiting less than a 75% soluble portion in the solubility test shall be considered to be substantially insoluble and of utility in the present process. Preferably, the derivatized polysaccharide with increased accessibility exhibits less than a 50% soluble portion in the solubility test, more preferably less than a 30% soluble portion in the solubility test.

Methods for derivatizing polysaccharides can be found in U.S. Pat. No. 8,602,994 B1 to Cash, et al., which is incorporated herein by reference in its entirety. Methods may include but are not limited to slurry and high solids processes typical of cellulose derivatization manufacture and can also include processes using equipment for alkaline treatment of lignocellulosics, including those commonly found in pulping, pulp washing and pulp bleaching operations.

Isolation of the derivatized polysaccharide having increased accessibility involves partial or complete removal of the swelling agent by various means.

A preferred method of isolation is to remove or neutralize the swelling agent from the slurry containing the derivatized polysaccharide with increased accessibility, with a washing agent. The conditions of the washing process as well as the composition of the washing agent may substantially impact the properties of the resulting derivatized polysaccharide. Among the washing process regimens that are of use in the present invention involve the use of water alone, water/alcohol mixtures or alcohols alone.

The derivatized polysaccharide with increased accessibility may be dried after the washing process. This may permit the storage of the derivatized polysaccharide with increased accessibility prior to its subsequent depolymerization to fermentable sugars. Alternatively, the derivatized polysaccharide with increased accessibility may be subsequently depolymerized by hydrolysis to fermentable sugars without being dried. This is a preferred process since the increased accessibility of the polysaccharide appears to be retained with an improvement in the yield of the fermentable sugars from the never dried polysaccharide with increased accessibility.

Enzyme Accessibility Test

In order to determine the degree of increased accessibility of a polysaccharide treated using the present process to enzyme when compared to a control polysaccharide, the enzyme accessibility test is performed. Any statistically significant increase in the soluble portion of initial solids of the polysaccharide when compared to an appropriate control as determined by the following test shall be considered to be indicative of a polysaccharide with increased accessibility. Please note, that the present test lists use of cellulase, since the polysaccharide being tested is cellulose. An appropriate enzyme should be selected for the particular polysaccharide being tested.

The below-listed amounts of samples and reagents may be varied to account for weighing accuracy and availability of materials.

The following is an example of the Enzyme Accessibility Test:
In 100 ml jars are added in order:
0.61 g Cellulase Enzyme (573 units*) Sigma EC 3.2.1.4 from *Pennicillum funiculosum* L#58H3291
 *1 unit=1 micromole of glucose from cellulose in 1 hour at pH 5 at 37° C. (as defined by Sigma-Aldrich for the enzyme used).
3.00 g cellulosic furnish (dry basis) such as cotton Sinters, wood pulp or biomass 75.00 g Sodium Phosphate buffer adjusted to pH 5.00, 50 milliMolar buffer. This buffer solution may be made by mixing 50 milliMolar monobasic and dibasic sodium phosphate buffers.
 (J.T. Baker Analyzed ACS Reagent grade, CAS#07558-79-4 and CAS#10049-21-5).
The jars are capped and shaken repeatedly over 5 minutes to disperse the mixture.
The jars are then placed in a 38° C. water bath and left overnight.
After cooling, the samples are centrifuged at 2000 RPM in a Fisher Marathon 3200 for 15 min.
The supernatant is decanted into a weighed aluminum pan.
The insolubles are rinsed twice with 25 ml room temperature distilled water.
The rinses are centrifuged as above and combined with the supernatant.
The combined supernatant and washes are dried to steady weight at 85° C. in a forced-air oven.
The insolubles are also dried in a weighed pan to steady weight at 85° C. in a forced-air oven.
The dried samples are weighed. A correction is made in the soluble portion for the weight of the buffer salts and for the weight of the enzyme added during the test.
Enzyme accessibility is calculated from this data as in the examples below. It is noted that variations in moisture content and slight variations in weighing precision can result in calculated results slightly above 100% or slightly below 0% in this method. The results shown in the following table are obtained without any correction for this type of method variance.
In the tables shown below data for five replicates are presented.
In the below test, an average of 95% of the untreated cellulose (cotton linters) remain insoluble.

| Cellulase g. | 0.0613 | 0.0607 | 0.0609 | 0.0611 | 0.0610 |
|---|---|---|---|---|---|
| Ccellulose (cotton linters) g. | 3.22 | 3.22 | 3.22 | 3.22 | 3.22 |
| Moist. Cont. | 11.42% | 11.42% | 11.42% | 11.42% | 11.42% |
| Dry furnish g. | 2.85 | 2.85 | 2.85 | 2.85 | 2.85 |

-continued

| | | | | | |
|---|---|---|---|---|---|
| All Solubles g. | 0.71 | 0.69 | 0.69 | 0.75 | 0.70 |
| Buffer Salts + Cellulase g. | 0.69 | 0.69 | 0.69 | 0.69 | 0.69 |
| Soluble Portion | 0.02 | 0.00 | 0.00 | 0.06 | 0.01 |
| % Soluble Portion | 0.7% | 0.0% | 0.0% | 2.1% | 0.4% |
| Dry Insolubles after washing g. | 2.72 | 2.72 | 2.71 | 2.69 | 2.75 |
| % Insoluble Portion | 95.4% | 95.4% | 95.0% | 94.3% | 96.4% |

| | Average | St. Dev |
|---|---|---|
| Total Solubles g. | 0.71 | 0.02 |
| Buffer Salts + Cellulase g. | 0.69 | 0.00 |
| Soluble Portion | 0.02 | 0.02 |
| % Soluble Portion | 0.63% | 0.87% |
| Dry Insolubles after washing g. | 2.72 | 0.02 |
| % Insoluble Portion | 95.3% | 0.76% |

In the below test, a 0.19 D.S. CMC exhibited increased solubility over the untreated cellulose controls listed in the previous table.

| | | | | | |
|---|---|---|---|---|---|
| Cellulase g. | 0.0607 | 0.0606 | 0.0599 | 0.0604 | 0.0603 |
| 0.19 D.S. CMC g. | 3.34 | 3.34 | 3.34 | 3.34 | 3.34 |
| Moist. Cont. | 11.60% | 11.60% | 11.60% | 11.60% | 11.60% |
| Dry furnish g. | 2.95 | 2.95 | 2.95 | 2.95 | 2.95 |
| All Solubles g. | 2.44 | 2.41 | 2.55 | 2.54 | 2.53 |
| Buffer Salts + Cellulase g. | 0.63 | 0.63 | 0.63 | 0.63 | 0.63 |
| Soluble Portion | 1.75 | 1.72 | 1.86 | 1.85 | 1.84 |
| % Soluble Portion | 59.2% | 58.2% | 63.0% | 62.6% | 62.3% |
| Dry insolubles after washing g. | 1.23 | 1.25 | 1.16 | 116 | 1.16 |
| % Insoluble Portion | 41.7% | 42.3% | 39.3% | 39.3% | 39.3% |
| D.S. | 0.19 | 0.19 | 0.19 | 0.19 | 0.19 |

| | Average | St. Dev |
|---|---|---|
| Total Solubles g. | 2.49 | 0.06 |
| Buffer Salts + Cellulase g. | 0.63 | 0.00 |
| Soluble Portion | 1.80 | 0.06 |
| % Soluble Portion | 61.09% | 2.19% |
| Dry Insolubles after washing g. | 1.19 | 0.04 |
| % Insoluble Portion | 40.4% | 1.50% |

A derivatized polysaccharide is considered to be a derivatized polysaccharide with increased accessibility if the increase in percent soluble portion as measured in this enzyme accessibility test is statistically significant in comparison with the polysaccharide control.

The soluble portion of initial solids of the derivatized polysaccharide with increased accessibility was 61.09% with a standard deviation of 2.19%. The soluble portion of the control polysaccharide was 0.63% with a standard deviation of 0.87%. The percentage greater accessibility of the treated polysaccharide would be (61.09/0.63) (100%)=9697%. Therefore this derivatized polysaccharide is considered to be a derivatized polysaccharide with increased accessibility.

Solubility Test

In order to determine the solubility of a polysaccharide, the Enzyme Accessibility Test as described hereinabove is performed without the addition of enzyme. Polysaccharides exhibiting less than a 75% soluble portion in the solubility test shall be considered to be substantially insoluble.

Standard Hydrolysis Process

Description of Standard Enzyme Hydrolysis Process

The impact of extent of polysaccharides with increased accessibility on enzyme availability has been studied by suspending sample cellulose fibers in water, adjusting pH as needed, adding a fixed amount of cellulase, mixing, and warming unstirred in a water bath for standard periods of time.

The derivatized polysaccharides with increased accessibility of this invention are subsequently depolymerized by hydrolysis under suitable conditions to produce fermentable sugars. Hydrolysis of the derivatized polysaccharide can be accomplished by treatment with acids, bases, steam or other thermal means, or enzymatically. Preferred methods of hydrolysis include treatment with enzymes, acids, or steam, with enzymatic hydrolysis being most preferred.

The fermentable sugars obtained by the above described process are then converted to target chemicals by enzymatic degradation such as occurs in fermentation.

One fermentation procedure consists simply of contacting the fermentable sugars under suitable fermentation conditions with yeast or related organisms or enzymes. Yeast contains enzymes which can use fermentable sugars, such as glucose, as an energy source and can be used to produce ethanol, water, and carbon dioxide as byproducts of the fermentation procedure. The carbon dioxide is released as a gas. The ethanol remains in the aqueous reaction media and can be removed and collected by any known procedure, such as distillation and purification, extraction, or membrane filtration. Other useful target chemicals may be likewise produced by fermentation.

The invention is further demonstrated by the following examples. The examples are presented to illustrate the invention, parts and percentages being by weight, unless otherwise indicated.

EXAMPLES

The examples used herein are listed below.

Table of Samples Shown in Examples

| Sample # | Furnish | Description | D.S. (CMC's) | M.S. (HEC's) | Used in Example |
|---|---|---|---|---|---|
| 1 | Cotton Linters | CMC | 0.73 | | Example 1 |
| 2 | Cotton Linters | Low DS CMC - Low NaOH Level | 0.14 | | Example 2 |
| 3 | Cotton Linters | Low D.S. CMC - High NaOH Level, with/without enzyme | 0.19 | | Examples 3, 8, 13 & Enzyme Accessibility Test |
| 4 | Cotton Linters | Process Control - No Chloroacetic Acid, Low NaOH | 0.00 | | Examples 4, 8, 13 |
| 5 | Wood Pulp VHV | Process Control - No EO, High NaOH | | 0.00 | Example 5 |
| 6 | Wood Pulp VHV | Process Control - No EO, High NaOH | | 0.00 | Example 5 |
| 7 | Wood Pulp VHV | HEC - High NaOH with/without enzyme | | 0.04 | Example 7 |
| 8 | Wood Pulp VHV | HEC - High NaOH with/without enzyme | | 0.06 | Example 7 |
| 9 | Wood Pulp VHV | HEC - High NaOH with/without enzyme | | 0.09 | Examples 5, 7 |
| 10 | Wood Pulp VHV | HEC - High NaOH with/without enzyme | | 0.27 | Examples 5, 7 |
| 11 | Wood Pulp VHV | HEC - High NaOH with/without enzyme | | 0.60 | Examples 5, 7 |

-continued

Table of Samples Shown in Examples

| Sample # | Furnish | Description | D.S. (CMC's) | M.S. (HEC's) | Used in Example |
|---|---|---|---|---|---|
| 12 | Wood Pulp Fluff | Process Control - No Chloroacetic Acid, High NaOH | 0.00 | | Example 6A |
| 13 | Wood Pulp Fluff | Low D.S. CMC - High NaOH Level, with/without enzyme | 0.08 | | Example 6A |
| 14 | Wood Pulp Fluff | Low D.S. CMC - High NaOH Level, with/without enzyme | 0.28 | | Example 6A |
| 15 | Wood Pulp Fluff | Low D.S. CMC - High NaOH Level, with/without enzyme | 0.29 | | Example 6A |
| 16 | Wood Pulp Fluff | Low D.S. CMC - High NaOH Level, with/without enzyme | 0.32 | | Example 6A |
| 17 | Wood Pulp Fluff | Low D.S. CMC - High NaOH Level, with/without enzyme | 0.36 | | Example 6A |
| 18 | Cotton Linters | Process Control - No Chloroacetic Acid, High NaOH | 0.00 | | Example 6B |
| 19 | Cotton Linters | Low D.S. CMC - High NaOH Level, with/without enzyme | 0.07 | | Example 6B |
| 20 | Cotton Linters | Low D.S. CMC - High NaOH Level, with/without enzyme | 0.05 | | Example 6B |
| 21 | Cotton Linters | Low D.S. CMC - High NaOH Level, with/without enzyme | 0.20 | | Example 6B |
| 22 | Cotton Linters | Commercial Cotton Linters | 0.00 | | Example 8 |
| 23 | Cotton Linters | Process Control - No Chloroacetic Acid, High NaOH | 0.00 | | Example 10 & Enzyme Accessibility Test |
| 24 | Wood Pulp Fluff | Process Control - No Chloroacetic Acid, High NaOH | 0.00 | | Example 10 |
| 25 | Wood Pulp Fluff | Low D.S. CMC - High NaOH Level, with/without enzyme | 0.15 | | Example 10 |
| 26 | L#91047 | Commercial CMC - AQUD 3949 from Hercules Incorporated | 0.78 | | Example 11 |
| 27 | L#91971 | Commercial CMC - AquaPAC ® from Hercules Incorporated | 1.06 | | Example 11 |
| 28 | Lot# 60764 | Commercial CMC - Blanose 7M65 ® from Hercules Incorporated | 0.73 | | Example 11 |
| 29 | Cotton Linters | Low DS CMC - Low NaOH Level | 0.22 | | Example 11, 13 |
| 30 | L#90604 | Commercial CMC - AQUD 3949 from Hercules Incorporated | 0.76 | | Example 6 |
| 31 | L#1701524 | Commercial CMC - IVH6 ® from Hercules Incorporated | 0.65 | | Example 6 |

Bottom of Table

Preparation of Derivatized Cellulose with Enhanced Accessibility

Example 1

Example of a Derivatized Cellulose Using Derivatization to a D.S. 0.78

In a 1-liter glass reactor with a water jacket attached to a circulating heating/cooling bath: A carboxymethyl cellulose (CMC) was produced using cotton linters as a cellulose source and following a standard protocol which consisted of adding 50% aqueous NaOH at approximately 20° C. to cellulose in an alcohol slurry. After stirring for a period of approximately one (1) hour, 50% monochloroacetic acid in isopropanol was added, and the stirred slurry was heated to 70° C. for more than an hour. The slurry was then cooled and filtered, and the resulting fibers were washed with approximately 20° C. aqueous alcohol for purification. The 50% isopropanol/chloroacetic acid solution and 50% NaOH solution amounts may be varied to meet the needs of a given run, in particular to control the D.S. The reaction conditions for Ex. 1 are set forth in Table 1.

TABLE 1

Sample #1

| | grams |
|---|---|
| Cotton Linters | 134.00 |
| IPA | 1327.8 |
| Water | 160.6 |
| NaOH (50% pure) | 142.52 |
| heat/cool to 20° C. and hold for 60 minutes | |
| IPA/MCA 50% | 158.85 |
| heat to 70° C. and hold 75 minutes cool | |

Example 2

Example of a Derivatized Cellulose Using Derivatization Conditions to Produce a Low D.S. CMC, D.S. 0.14, Using Lower Levels of Swelling Agent Similarly, runs were made using essentially the same ratios of ingredients as in Example 1 except for the relative amounts of MCA and NaOH were reduced to give low D.S. CMC. The reaction conditions for Example 2 are set forth in Table 2.

TABLE 2

Sample #2

| | grams |
|---|---|
| Cotton Linters | 123.82 |
| IPA | 1488.97 |
| Water | 223.40 |
| NaOH (50% pure) | 90.33 |
| heat/cool to 20° C. and hold for 60 minutes | |
| IPA/MCA 50% | 44.385 |
| heat to 70° C. and hold 90 minutes | |
| cool | |

Example 3

Example of a Derivatized Cellulose Using Derivatization Conditions to Produce a Low D.S. CMC, D.S. 0.194, Using Higher Levels of Swelling Agent Additionally, runs were made using only lower ratios of MCA with a higher level of NaOH. The reaction conditions for Example 3 are set forth in Table 3.

TABLE 3

Sample #3

| | grams |
|---|---|
| Cotton Linters | 67.002 |
| IPA | 663.9 |
| Water | 80.30 |
| NaOH (50% pure) | 71.34 |
| heat/cool to 20° C. and hold for 60 minutes | |
| IPA/MCA 50% | 22.05 |
| heat to 70° C. and hold 75 minutes | |
| cool | |

Example 4

Comparative

Example of Caustic Treated Cellulose Control, D.S. 0.00

As a control, runs were made using the entire process as set forth in Examples 1 to 3 except the addition of the derivatizing agent (MCA) was eliminated. This example compares the effect of NaOH alone on cellulose when subjected to the thermal cycle of the process to produce the CMCs of Examples 1-3. The reaction conditions for Example 4 (Comparative) are set forth in Table 4.

TABLE 4

Sample #4

| | grams |
|---|---|
| Cotton Linters | 61.90 |
| IPA | 774.50 |
| Water | 111.71 |
| NaOH (50% pure) | 20.03 |
| heat/cool to 20° C. and hold for 60 minutes | |

TABLE 4-continued

Sample #4

| | grams |
|---|---|
| IPA | 22.10 |
| heat to 70° C. and hold 75 minutes | |
| cool | |

Example 5

A Derivatized Cellulose Using Derivatization Conditions to Produce a Hydroxyethylcellulose (HEC)

Hydroxyethylcellulose (HEC) was made from a dissolving wood pulp, (Borregaard VHV, available from Borregaard ChemCeil, Sarpsborg, Norway).

In a 2-liter steel reactor with a heating/cooling Huber thermostat:

A hydroxyethyl cellulose (HEC) was produced under nitrogen using wood pulp as a cellulose source and following a standard protocol which consisted of adding 40% aqueous NaOH to cellulose in an alcohol slurry at about 20° C. After stirring for a period, usually between thirty minutes and one hour, ethylene oxide was added, and the stirred slurry was heated to 45° C. for 45 minutes, and then heated to 90° C. for an hour. The slurry was then cooled and filtered, and the resulting fibers were washed with aqueous acetone for purification. The ethylene oxide and 40% NaOH solution amounts may be varied to meet the needs of a given run.

The HEC was made in several runs at levels of molar substitution (MS) including MS=0.0, MS=0.27, and MS=0.60 at varying levels of ethylene oxide to obtain reduced levels of hydroxyethylation in the resultant HEC. The products were purified by normal HEC production procedures.

The resulting powders were tested using the Enzyme Accessibility Test, as described hereinabove. Samples of HEC and two wood pulp controls were run in matched pairs through the Enzyme Accessibility Test. Each sample contained 3 grams of cellulosic in 50 millimolar Sodium Phosphate buffer at pH 5.00 at 37° C. overnight. The Sodium Phosphate was a mixture of the monobasic and dibasic salts (available from J. T. Baker) and was blended to obtain the desired pH. The soluble and insoluble fractions, prepared both with and without cellulase, were dried and the enzyme hydrolysis results compared for the untreated and treated pairs. Results are shown in Table 5.

TABLE 5

Enzyme Accessibility Test of HEC samples of Example 5

| | Wood Pulp | Wood Pulp | Low M.S. HEC | Low M.S. HEC |
|---|---|---|---|---|
| MS of HEC | 0.00 | 0.00 | 0.27 | 0.60 |
| % Insolubles without enzyme | 88% | 98% | 93% | 86% |
| % Insolubles with enzyme | 82% | 78% | 42% | 5% |
| % Solubles without enzyme | 7% | 3% | 5% | 12% |

TABLE 5-continued

Enzyme Accessibility Test of HEC samples of Example 5

|  | Wood Pulp | Wood Pulp | Low M.S. HEC | Low M.S. HEC |
|---|---|---|---|---|
| % Solubles with enzyme | 17% Sample #5 | 22% Sample #6 | 53% Sample #10 | 96% Sample #11 |

As is shown in the Table 5, low M.S. HECs of Example 5 have improved enzyme hydrolysis availabilities of 53% and 98% as determined in the Enzyme Accessibility Test as compared with the two wood pulp controls, which were not derivatized, which averaged about 20% solubilized.

Example 6

The Impact of Degree of Substitution (D.S.) on Solubility vs. Enzyme Accessibility of Polysaccharides Using the Enzyme Accessibility Test, as described hereinabove, a series of low D.S. CMC samples were treated to determine the effect of variation in D.S. on their water solubility and enzyme accessibility. The D.S. levels of the derivatized celluloses were at D.S. levels below the levels which would impart water solubility to the derivatized cellulose polymer, in the first series of samples, the polysaccharide was a cellulose obtained from wood. The low D.S. CMC's were made from wood pulp (Foley Fluff wood pulp, available from Buckeye Technologies Inc., Memphis, Tenn.).

Samples were prepared in matched pairs with and without cellulase enzyme. 2.00 g (corrected for moisture content) of the CMC sample was mixed with 50.0 g pH 5.0 sodium phosphate and shaken. The remainder of the procedure is described in the Enzyme Accessibility Test. Some samples thickened to the point where the insolubles could not be separated from the soluble fraction by the centrifugation used in the test, and are described in Table 6 as 'gel-like'. For these samples the insoluble fraction remained and was obtainable by this test after enzyme treatment.

TABLE 6A

D.S. Impact on Solubility vs. Accessibility for CMC Produced From Wood Pulp

| Sample D.S. by Ash | 0.00 | 0.08 | 0.28 | 0.29 | 0.32 | 0.36 |
|---|---|---|---|---|---|---|
| % Soluble without enzyme | 2.87 | 12.55 | 28.15 | 23.11 | "gel-like" | "gel-like" |
| % Soluble with enzyme | 18.37 | 23.63 | 64.51 | 83.32 | 81.12 | 97.47 |
|  | Sample #12 | Sample #13 | Sample #14 | Sample #15 | Sample #16 | Sample #17 |

Similarly, in the second series of samples, the polysaccharide was a cellulose obtained from cotton linters to produce samples of low D.S. CMC which exhibit enhanced enzyme accessibility compared to their water solubility. CMC's were made using cotton linters (Southern 407 linters available from ADM-Southern Cotton Oil Company, Georgia). The samples were prepared as above.

TABLE 6B

D.S. Impact on Solubility vs. Accessibility for CMC Produced From Cotton Linters

| Sample D.S. by Ash | 0.00 | 0.05 | 0.07 | 0.20 |
|---|---|---|---|---|
| % Soluble without enzyme | 0.00 | 5.00 | 5.00 | 7.00 |

TABLE 6B-continued

D.S. Impact on Solubility vs. Accessibility for CMC Produced From Cotton Linters

| % Soluble with enzyme | 7.00 Sample #18 | 10.00 Sample #19 | 13.50 Sample #20 | 61.50 Sample #21 |
|---|---|---|---|---|

The samples of Example 6 are represented in FIG. 1. In FIG. 1, it is depicted that the increase in the accessibility of the derivatized cellulose to enzyme occurs at a lower level of derivatization than its solubility in water. This difference between the derivatized polysaccharide increased accessibility, and its solubility, is a benefit of the present invention for it permits the production of derivatized polysaccharides with increased accessibility to hydrolysis, while maintaining the derivatized polysaccharide in a relatively insoluble state.

Example 7

D.S. Impact on Solubility vs. Accessibility

HEC

Using the Enzyme Accessibility Test, as described hereinabove, a series of low M.S. HEC was treated to determine the effect of variation in M.S. on water solubility and enzyme accessibility at M.S. levels below the levels which would impart water solubility to the derivatized cellulose polymer. Hydroxyethylcellulose (HEC) was made from a dissolving wood pulp, (Borregaard VHV available from Borregaard ChemCeil, Sarpsborg, Norway). The HEC was made at various low levels of molar substitution (MS) using a recipe similar to that used for commercial HEC products except for the use of reduced levels of ethylene oxide. These reduced levels of ethylene oxide resulted in reduced levels of hydroxyethylation in the resultant HEC samples. The samples were purified by normal HEC production procedures.

Samples were prepared in matched pairs with and without cellulase enzyme. 3.00 g (corrected for moisture content) of the HEC sample was mixed with 50.0 g pH 5.0 sodium phosphate and shaken. The remainder of the procedure is described in the Enzyme Accessibility Test.

TABLE 7

M.S. impact on Solubility vs. Accessibility for HEC Produced from Wood Pulp

| Sample MS | 0.00 | 0.04 | 0.06 | 0.09 | 0.27 | 0.60 |
|---|---|---|---|---|---|---|
| % Soluble without enzyme | 3.4 | 4.1 | 2.7 | 5.9 | 4.5 | 12.4 |
| % Soluble with enzyme | 22.2 | 19.3 | 27.4 | 18.8 | 53.0 | 95.9 |
|  | Sample #6 | Sample #7 | Sample #8 | Sample #9 | Sample #10 | Sample #11 |

Example 8

X-Ray Powder Diffraction Data for Low D.S. CMCs

Samples of Low D.S. CMCs shown in Example 6 were submitted for X-Ray powder diffraction analysis (XRD) to determine relative levels of ordering. In addition, published pattern data were obtained for Cellulose I and Cellulose II. This shows peaks for Cellulose I at 2-Theta angles of 14.9, 16.8, 23.7, and 34.6. Peaks for Cellulose II are found at 2-Theta angles of 12.3, 20.0, 21.9, and 34.6.

XRD analysis was performed using a Shimadzu Lab X. XRD 6000; sampled from 4 to 45 degrees two-Theta.

As shown in Table 8, the non-derivatized cellulose samples based on cotton linters, both before and after the Enzyme Accessibility Test, gave easily assignable Cellulose I peaks. The low D.S. CMC, an example of a derivatized polysaccharide with increased accessibility, instead gave a single peak typical of amorphous scattering as reported below.

TABLE 8

X-Ray Powder Diffraction Data for Low D.S. CMCs

|  | Commercial Cotton Linters D.S. = 0.00 | Linters after Accessibility Test D.S. = 0.00 | Low D.S. CMC D.S. = 0.20 |
|---|---|---|---|
| Peak @ 2-Theta 15.3° - Relative Intensity | 32 | 26 | None |
| Peak @ 2-Theta 15.3° - Crystallite Size Å | 36.6 | 43.7 | None |
| Peak @ 2-Theta 16.6° - Relative Intensity | 28 | 23 | None |
| Peak @ 2-Theta 16.6° - Crystallite Size Å | 34.2 | 37.4 | None |
| Peak @ 2-Theta 22.9° - Relative Intensity | 100 | 100 | None |
| Peak @ 2-Theta 22.9° - Crystallite Size Å | 49.7 | 51.9 | None |
| Peak @ 2-Theta 34.6° - Relative Intensity | 6 | 6 | None |
| Peak @ 2-Theta 22.9° - Crystallite Size Å | 47.8 | 50.4 | None |
| Peak @ 2-Theta 20.4° - Relative Intensity | None | None | 100 |
| Peak @ 2-Theta 20.4° - Crystallite Size Å | None | None | Amorphous |
|  | Sample #22 | Sample #4 | Sample #3 |

Example 9

X-Ray Powder Diffraction Data for Low M.S. HECs

Samples of Low M.S. HECs shown in Example 5 were submitted for X-Ray powder diffraction analysis (XRD) to determine relative levels of ordering. In addition, published pattern data were obtained for Cellulose I and Cellulose II. This shows peaks for Cellulose I at 2-Theta angles of 14.9, 16.6, 23.7, and 34.6. Peaks for Cellulose II are found at 2-Theta angles of 12.3, 20.0, 21.9, and 34.6.

XRD was performed using a Shimadzu Lab X, XRD 6000; sampled from 4 to 45 degrees two-Theta.

TABLE 9

X-Ray Powder Diffraction Data for Low MS HECs

| Approximate Peak Maximum Angle | Wood Pulp after Accessibility Test M.S. = 0.00 | Low M.S. HEC M.S. = 0.09 | Low M.S. HEC M.S. = 0.27 | Low M.S. HEC D.S. = 0.60 |
|---|---|---|---|---|
| Cellulose I Peaks: | | | | |
| Peak @ 2-Theta 10.0° - Relative Intensity | None | None | 17 | 9 |
| Peak @ 2-Theta 10.0° - Crystallite Size Å | None | None | Peak too small to measure | Peak too small to measure |
| Peak @ 2-Theta 15.5° - Relative Intensity | 14 | 7 | None | None |
| Peak @ 2-Theta 15.5° - Crystallite Size Å | 35.2 | Peak too small to measure | None | None |
| Peak @ 2-Theta 22.2° - Relative Intensity | 100 | 100 | None | None |
| Peak @ 2-Theta 22.2° - Crystallite Size Å | 31.9 | 37.9 | None | None |
| Peak @ 2-Theta 34.6° - Relative Intensity | 6 | None | None | None |
| Peak @ 2-Theta 34.6° - Crystallite Size Å | Peak too small to measure | None | None | None |
| Cellulose II Peak: | | | | |
| Peak @ 2-Theta 20.8° - Relative Intensity | None | 77 | 100 | 100 |
| Peak @ 2-Theta 20.8° - Crystallite Size Å | None | 42.1 | Amorphous | Amorphous |
|  | Sample # 5 | Sample # 9 | Sample # 10 | Sample #11 |

As shown in Table 9, the wood pulp samples both before and after the Enzyme Accessibility Test gave easily assignable Cellulose I peaks. The low M.S. HEC was determined to be amorphous at a Peak @2-Theta 20.8°—Crystallite Size Å.

Example 10

Acid Hydrolysis

Two pairs of samples were used, a low D.S. CMC produced from wood pulp, a low D.S. CMC produced from cotton Sinters, and their respective 0.0 D.S. controls which had been run through the same reaction conditions without any addition of chloroacetic acid as the derivatization agent.

CMC's of this Example were made in a one liter scale laboratory reactor at a ratio of 2.15 moles of sodium hydroxide per mole of anhydroglucose sugar monomer unit (as wood pulp and cotton linter fibers in an alcohol/water slurry).

Four (4) dry grams of each CMC sample was treated with 50.0 grams of 2.5 Molar hydrochloric acid and heated to 50° C. for four hours. The samples were then left overnight capped at room temperature, neutralized to pH 6.5 to pH 7.5 with sodium hydroxide, and filtered. The wetcake was re-slurried three times in 50 ml portions of distilled water and re-filtered. The insoluble wetcakes were oven dried to steady weight at 85° C. in a VWR 1350FD forced-air oven. Both samples of low D.S. CMC proved harder to filter than the controls due to the release of fine particles from the fibers, and partial swelling in the case of the CMC made from cotton linters. For its last rinse, the low D.S. CMC produced from cotton linters had to be centrifuged to remove by decantation the last of the residual salt of neutralization.

TABLE 10

Acid Hydrolysis of CMCs

|  | Wood Pulp | Wood Pulp | Cotton Linter | Cotton Linter |
|---|---|---|---|---|
| D.S. of CMC | 0.00 | 0.15 | 0.00 | 0.19 |
| Sample weight added g | 3.26 | 3.16 | 3.21 | 3.34 |
| Moisture Content % | 8.73 | 5.48 | 6.99 | 11.42 |
| Sample dry weight g | 3.00 | 3.00 | 3.00 | 3.00 |
| Dry Weight after Hydrolysis | 2.85 | 2.39 | 2.94 | 2.43 |
| % Solubles (calculated) | 5.00% | 20.33% | 2.00% | 19.00% |
| % Insolubles | 95.00% | 79.67% | 98.00% | 81.00% |
| % Improvement in Solubles | 0.00% | 306.67% | 0.00% | 850.00% |
|  | Sample #24 | Sample #25 | Sample #3 | Sample #23 |

As the results in Table 10 show, the insoluble fraction was greatly reduced in the low D.S. CMCs compared with their 0.0 D.S. controls, and the % solubles calculated by difference was greatly increased. This demonstrates that the improvement in hydrolysis was not limited to enzymatic hydrolysis but was also demonstrated in acid hydrolysis. Therefore, the improvement in hydrolysis of the derivatized polysaccharide with enhanced accessibility may be independent of the mode of hydrolysis employed.

Example 11

Production of Target Chemicals from Derivatized Cellulose

In these examples, cellulose was derivatized to a Degree of Substitution (D.S.) of about 0.10 to 0.3 per anhydroglucose (AHG) repeat unit of the cellulose polymer.

Once a derivatized cellulose substrate was enzyme treated with cellulase to produce glucose by hydrolysis, yeast was applied to the resulting slurry to demonstrate that the solubilized glucose, produced from the derivatized cellulose substrate was in fact fermentable sugars and comprise a suitable substrate for yeast fermentation into target chemicals, such as ethanol. Following a two hour cellulase treatment, dry yeast was added, and the bottle sample was heated in the 50° C. bath for two more hours and left at room temperature overnight. After yeast treatment, the slurry was centrifuged. The supernatant was collected and a portion dried to determine the non-volatile soluble fraction, presumably soluble sugars and residual enzyme. The wet solids from centrifugation were washed several times and dried to determine the insoluble fraction remaining after combined cellulase and yeast treatment. A mass balance was determined by difference to estimate the amount of volatile materials produced. The majority of the volatile materials are presumed $CO_2$, as well as ethanol, as evidenced by the perceived sweet ethanol odor.

Table 11 demonstrates a set of cellulose with increased accessibility samples taken through the two steps described above. Suitable controls that are examples of a cellulose without increased accessibility are provided for comparison. In this case, conditions were 40° C. for two hours in the cellulase stage, and 14 hours at 40° C. in the yeast stage, it was known that higher levels of sodium hydroxide causes increased swelling of cellulose up to levels known as mercerizing conditions. Sample 11B used a low level of NaOH, while sample 11A used a level near the mercerization condition. The higher caustic sample had about 7% residual solids after combined cellulase and yeast treatment, compared to 46% for the sample with less NaOH.

TABLE 11

| Designation | 11A | 11B | 11C | Comp. 11A | 11D | 11E |
|---|---|---|---|---|---|---|
| Cellulase (g) | 0.10 | 0.10 | 0.10 | 0.10 | 0.10 | 0.10 |
| furnsh (g) | 5.00 | 5.00 | 5.00 | 5.00 | 5.00 | 5..0 |
| yeast (g) | 0.25 | 0.25 | 0.25 | 0.25 | 0.25 | 0.25 |
| Moist. Cont. | 6.09 | 5.60% | 9.49% | 4.28% | 11.92% | 7.76% |
| Dry furnish (g) | 4.70 | 4.72 | 4.53 | 4.79 | 4.40 | 4.61 |
| residual solids (g) | 0.36 | 2.32 | 0.24 | 3.92 | 0.28 | 0.27 |
| % of initial solids | 7.14% | 45.76% | 4.92% | 76.32% | 5.89% | 5.44% |
| % solubilized | 92.86% | 54.24% | 95.08% | 23.68% | 94.11% | 94.56% |
| D.S. by Ash | 0.19 | 0.22 | 0.78 | 0 | 1.06 | 0.73 |
|  | Sample #3 | Sample # 29 | Sample #26 | Sample #4 | Sample #27 | Sample #28 |

From Table 11, it was noted that the low D.S., low caustic material 11B, was not completely converted to ethanol, even after derivatization. The low D.S., low caustic material cited in Table 11 is an example of cellulose prepared using derivatization reaction conditions that provide improved but not complete accessibility of the cellulosic substrate during the alkali cellulose stage. In contrast, the low D.S., high NaOH material was almost completely converted.

Example 12

Production of Target Chemicals from Derivatized Cellulose, Post Hydrolysis Fermentation In the process described in Table 5, a fresh set of samples was obtained and subsequent step of adding baking yeast after the hydrolysis to make a "beer" from the resulting sugar solutions (and the un-dissolved "mash" of fibers), thus obtaining ethanol. Both derivatized and underivatized cellulose furnish were treated with cellulase and yeast.

TABLE 12

| | Designation | | | |
|---|---|---|---|---|
| | Comp. 12A | 12A | 12B | 12C |
| | | Source | | |
| | Lab | Lab | Commercial | Commercial |
| DS | 0.00 | 0.22 | 0.76 | 0.65 |
| Cellulase | 0.10 g | 0.10 g | 0.10 g | 0.10 g |
| g furnish | 5.00 | 5.00 | 5.00 | 5.00 |
| Moist. Cont. | 4.79% | 4.66% | 9.49% | 7.12% |
| Dry g furnish | 4.76 | 4.77 | 4.53 | 4.64 |
| pH of mixture | 4.82 | 5.15 | 5.21 | 5.47 |
| Red Star Yeast g dry | 0.25 | 0.25 | 0.25 | 0.25 |
| residual solids** g | 4.23 | 2.52 | 0.09 | 0.021 |
| % Insolubles after fermentation | 88.86% | 52.86% | 1.99% | 0.45% |
| % Solubles | 11.14% | 47.14% | 98.01% | 99.55% |
| Filtrate solids g | 0.15 | 0.67 | 1.10 | 1.17 |
| Solids per 95 g | 0.23 | 0.83 | 1.07 | 1.12 |
| % Soluble Sugars after ferm. | 4.83% | 17.41% | 23.64% | 24.12% |
| Material Balance | 93.69% | 70.27% | 25.63% | 24.57% |
| Est. Volatiles by Difference | 6% | 30% | 74% | 75% |
| | Sample #4 | Sample #29 | Sample #30 | Sample #31 |

Underivatized cellulose (Comp. 12A) has about 88.86% insoluble following the combined enzyme treatments. By contrast, DS=0.22 CMC (12A) has about 52.86% insoluble material. The decrease in residual insoluble material, as well as the overall mass balance recovery of only about 70%. The presence of both glucose and ethanol in all soluble fractions after yeast treatment was confirmed by proton NMR. The ethanol $CH_3$ peak was observed at 1.15 ppm and the ethanol $CH_2$ and glucose protons overlap in the region of 3.2 to 5 ppm.

Example 13

Production of Fermentable Sugars from Derivatized Cellulose, Hydrolysis by Various Enzymes In this example the amount of glucose generated following enzyme treatment, from either a derivatized cellulose, or a control cellulose that was swollen but not derivatized, for several different types of cellulase enzymes, was determined. Results are tabulated in Table 13.

TABLE 13

| | | Time in Minutes | | | | |
|---|---|---|---|---|---|---|
| Sample # | Enzyme System | 120 | 210 | 300 | 405 | 1500 |
| | | | | Glucose, %[1] | | |
| 29 | Celluclast | 6.73 | 9.26 | 10.86 | 14.02 | |
| 29 | Carezyme | −0.13 | 0.23 | 0.36 | 0.80 | 8.85 |
| 3 | Celluclast | 18.19 | 23.63 | 29.64 | 32.58 | |
| 3 | Carezyme | 0.00 | 0.36 | 1.70 | 2.45 | 8.85 |
| 4 | Celluclast | 0.67 | 0.73 | 3.22 | 4.18 | |
| 4 | Carezyme | −0.18 | 0.05 | 0.00 | 0.09 | 0.40 |

[1]Glucose, % - refers to the percentage of the initial solids as glucose

For this work glucose was determined using a spectrophotometric method. 25.0 ml of buffer solution (100 mM sodium phosphate) along with a stirring bar was placed on a magnetic stirrer and stirred at room temperature. After reaching temperature, an aliquot of enzyme was added followed by 50 mg of sample at time 0. Aliquots (50 µl) were removed at specific intervals and analyzed using a standard assay for glucose. For the assay 1.5 ml GOPOD (glucose oxidase and peroxidase) reagent was added to the sample, incubated at 45° C. for 20 min. Absorbance at 510 nm was read and adjusted for the absorbance of a blank to obtain D-glucose concentration. Enzymes evaluated included Celluclast 1.5L (Novozymes—*Trichoderma reesei*), a mixture of exo- and endo-cellulases and Carezyme 1000L (Novozymes—from *Aspergillus* species), an endo-cellulase.

The results demonstrate that the initial rate of fermentable sugar production, in this case glucose, from a derivatized cellulose, compared to an underivatized cellulose, is significantly increased. This is true for both forms of cellulase evaluated demonstrating that improved enzyme accessibility is evident for a variety of hydrolytic enzymes. The enzyme level used for this evaluation represents a low dosage of enzyme compared to the Enzyme Accessibility Test It is not intended that the examples given here should be construed to limit the invention, but rather they are submitted to illustrate some of the specific embodiments of the invention. Various modifications and variations of the present invention can be made without departing from the scope of the appended claims.

We claim:

1. A process for producing fermentable sugars from polysaccharide containing biomass, comprising the steps of:
   treating the biomass with a swelling agent to produce a swelled biomass;
   contacting the swelled biomass with a derivatization agent to derivatize the polysaccharide contained therein to produce a derivatized polysaccharide with increased accessibility, wherein the derivatized polysaccharide, as compared to a swelled polysaccharide without derivatization, (i) exhibits an increase in a soluble portion as determined by an Enzyme Accessibility Test, and (ii) is substantially insoluble as measured by a Solubility Test; and
   converting the derivatized polysaccharide to fermentable sugars by hydrolysis;
   fermenting the fermentable sugars with at least one biocatalyst under suitable fermenting conditions to produce a target chemical;
   converting a portion of the target chemical into at least one derivatization agent; and
   feeding at least a portion of the converted derivatization agent back into the step of contacting the swelled biomass with a derivatization agent.

2. The process of claim 1, further comprising the step of removing the swelling agent after the biomass is contacted with the derivatization agent.

3. The process of claim 1, wherein the derivatization agent reacts with at least one of a hydroxyl, carboxyl, and other functional groups of the polysaccharide to form a derivatized polysaccharide having a degree of substitution greater than 0.1.

4. The process of claim 3, wherein the derivatized polysaccharide has a degree of substitution in a range of from about 0.1 to about 1.2.

5. The process of claim 3, wherein the derivatized polysaccharide has a degree of substitution in a range of from about 0.1 to about 0.6.

6. The process of claim 3, wherein the derivatized polysaccharide is selected from the group consisting of hydroxyethyl cellulose, ethylhydroxyethyl cellulose, carboxymethylcellulose, carboxymethylhydroxyethyl cellulose, hydroxypropylhydroxyethyl cellulose, methyl cellulose, methylhydroxypropyl cellulose, methylhydroxyethyl cellulose, carboxymethylmethyl cellulose, hydrophobically modified carboxymethyl cellulose, hydrophobically modified hydroxyethyl cellulose, hydrophobically modified hydroxypropyl cellulose, hydrophobically modified ethylhydroxyethyl cellulose, hydrophobically modified carboxymethylhydroxyethyl cellulose, hydrophobically modified hydroxypropylhydroxyethyl cellulose, hydrophobically modified methyl cellulose, hydrophobically modified methylhydroxypropyl cellulose, hydrophobically modified methylhydroxyethyl cellulose, hydrophobically modified carboxymethylmethyl cellulose, nitrocellulose, cellulose acetate, cellulose sulfate, cellulose vinyl sulfate, cellulose phosphate, methylol cellulose, cellulose phosphonate, and combinations thereof.

7. The process of claim 6, wherein the derivatized polysaccharide is carboxymethylcellulose.

8. The process of claim 7, wherein the carboxymethylcellulose has a degree of substitution in a range of from about 0.1 to about 0.6.

9. The process of claim 6, wherein the derivatized polysaccharide is hydroxyethylcellulose.

10. The process of claim 9, wherein the hydroxyethylcellulose has a molar substitution in a range of from about 0.1 to about 2.0.

11. The process of claim 1, wherein the derivatization agent is selected from the group consisting of chloroacetic acid, sodium chloroacetate, alkyl halides, anhydrides, aldehydes, compounds containing quaternary cation functionality, epichlorhydrin, and mixtures thereof.

12. The process of claim 11, wherein the derivatization agent is ethylene oxide.

13. The process of claim 1, wherein the derivatization agent is at least one of chloroacetic acid and sodium chloroacetate.

14. The process of claim 1, wherein the derivatized polysaccharide has a molar substitution in a range of from about 0.1 to about 3.0.

15. The process of claim 14, wherein the derivatized polysaccharide has a molar substitution of less than about 1.5.

16. The process of claim 14, wherein the derivatized polysaccharide has a molar substitution of less than about 1.0.

17. The process of claim 1, wherein the biomass comprises cellulose and the fermentable sugars comprise glucose.

18. The process of claim 1, wherein the step of converting the derivatized polysaccharide to fermentable sugars by hydrolysis comprises the step of contacting the derivatized polysaccharide with at least one saccharification enzyme under suitable conditions to produce the fermentable sugars.

19. The process of claim 1, wherein the step of converting the derivatized polysaccharide to fermentable sugars by hydrolysis comprises the step of acid hydrolysis of the derivatized polysaccharide to produce the fermentable sugars.

20. The process of claim 1, wherein the polysaccharide contained within the biomass is selected from the group consisting of cellulose, hemicellulose, chitin, chitosan, guar gum, pectin, alginate, agar, xanthan, starch, amylose, amylopectin, alternan, gellan, mutan, dextran, pullulan, fructan, locust bean gum, carrageenan, glycogen, glycosaminoglycans, murein, bacterial capsular polysaccharides, and combinations thereof.

21. The process of claim 20, wherein the polysaccharide is cellulose.

22. The process of claim 1, wherein the biomass is selected from the group consisting of bioenergy crops, agricultural residues, municipal solid waste, industrial solid waste, sludge from paper manufacturer, yard waste, wood and forestry waste, bamboo, bagasse, flax, hemp, manila hemp, sisal hemp, jute, ramie, kanif corn grain, corn cobs, crop residues, corn husks, corn stover, grasses, wheat, wheat straw, barley, barley straw, hay, rice straw, cotton, cotton linters, switchgrass, post consumer paper, post consumer paperboard, sugar cane bagasse, sorghum, soy, components obtained from milling of grains, trees, branches, roots, leaves, wood chips, sawdust, wood pulp, shrubs and bushes, vegetables, fruits, flowers, animal manure, bacteria, algae, fungi, and combinations thereof.

23. The process of claim 1, wherein the swelling agent is selected from the group consisting of alkali metal oxides, alkali metal hydroxides, alkaline earth metal oxides, alkaline earth metal hydroxides, alkali silicates, alkali aluminates, alkali carbonates, amines, ammonia, ammonium hydroxide, tetramethyl ammonium hydroxide, lithium chloride, N-methyl morpholine N-oxide, urea, and mixtures thereof.

24. The process of claim 23, wherein the swelling agent is at least one of sodium hydroxide and ammonium hydroxide.

25. The process of claim 1, further comprising the step of neutralizing the swelling agent after the biomass is contacted with the derivatization agent.

26. The process of claim 1, wherein the target chemical is selected from the group consisting of alcohols, aldehydes, ketones, acids, and combinations thereof.

27. The process of claim 26, wherein the target chemical is alcohol.

28. The process of claim 27, wherein the alcohol is ethanol.

29. The process of claim 27, wherein the alcohol is butanol.

30. The process of claim 29, wherein butanol is at least one of n-butanol, sec-butanol, isobutanol, tert-butanol, and combinations thereof.

31. The process of claim 1, wherein the target chemical is ethanol and the derivatization agent is ethylene oxide.

32. The process of claim 1, wherein the swelled biomass has disrupted intramolecular and intermolecular hydrogen bonds therein.

33. The process of claim 1, wherein the derivatized polysaccharide is substantially in the amorphous phase.

34. The process of claim 1, wherein the derivatized polysaccharide has a solubility of less than 75%, as measured by the Solubility Test.

* * * * *